United States Patent [19]

Dye

[11] Patent Number: 4,759,313
[45] Date of Patent: Jul. 26, 1988

[54] ETHYLENE OXIDE PROCESS IMPROVEMENT

[75] Inventor: Robert F. Dye, Sugar Land, Tex.

[73] Assignee: Shell Oil Company, Houston, Tex.

[21] Appl. No.: 115,685

[22] Filed: Oct. 30, 1987

[51] Int. Cl.$^4$ .............................................. F22B 1/02
[52] U.S. Cl. ....................................... 122/32; 122/34; 165/1
[58] Field of Search ...................... 122/32, 33, 34, 7 R; 165/1

[56] References Cited

U.S. PATENT DOCUMENTS 2,823,650  2/1958  Hedback et al. ........................ 122/32
4,074,660  2/1978  Tsau ...................................... 122/32
4,482,004  11/1984 Grover ............................... 122/33 X Primary Examiner—Edward G. Favors
Attorney, Agent, or Firm—Y. Grace Tsang

[57] ABSTRACT

An improved ethylene oxide process whereby residual heat is recovered from the reactor coolant by generating steam. The improvement enables the plant to operate using an improved silver-based catalyst with lower optimum operating temperature than that of the alumina-supported silver catalyst for which the plant was designed. The process comprises the steps of passing the coolant from the reactor to at least one first coolant condenser(s) wherein at least part of the coolant vapor is condensed by exchanging heat with boiler feed water to generate steam. The vapor-liquid two-phase stream coming out of said first coolant condenser(s) is passed through a vapor-liquid separator whereby the liquid coolant is separated from the coolant vapor and flows via a "U" trap to coolant surge drum(s) and the coolant vapor passes through a second condenser(s) adapted for generating steam with a lower pressure than that of the steam generated by said first coolant condenser; wherein said "U" trap has a sufficient height to insure that the coolant vapor flows upward to said second coolant condenser(s).

8 Claims, 1 Drawing Sheet

ETHYLENE OXIDE PROCESS IMPROVEMENT

FIELD OF THE INVENTION

The present invention relates to an improved ethylene oxide process whereby residual heat is recovered from the reactor coolant by generating steam, with additional steam being produced by an auxiliary coolant condensing system that requires no operator attention.

BACKGROUND OF THE INVENTION

There has been continuous improvement in ethylene oxide catalysts in the past twenty years, particularly with respect to improvements in selectivity, activity and stability. Ethylene oxide/ethylene glycol (EO/EG) plants are usually designed for a particular ethylene oxide catalyst. If an improved catalyst utilizes a lower optimum operating temperature, the plant can not take the full advantage of the improvement, e.g., a catalyst with higher activity and lower optimum operating temperature may fail to generate enough medium or lower-pressure steam to meet the requirements for the operation of the plant. Steam is utilized as heating source for various equipment in EO/EG plants. When the operating temperature in the reactor is lower, the temperature of the coolant in the coolant condenser is also lower. The temperature difference ($\Delta T$) between the coolant and the steam generated in the steam generator drops. The surface area of the coolant condenser is fixed in a conventional EO/EG plant designed for a particular catalyst. Thus, the amount of medium-pressure steam generated would be reduced by a lower $\Delta T$.

To avoid the cost of adding a steam generator to make up the loss in steam production when operating with an improved catalyst which has a lower optimum operating temperature than the catalyst for which the plant was designed, the reactor would have to be operated at a temperature higher than the optimum operating temperature in order to raise the coolant temperature to one providing a sufficient $\Delta T$ for generating enough medium-pressure steam. Since the reaction would not be operated at the optimum temperature of the catalyst, the selectivity decline rate would be accelerated. Such an accelerated decline could eventually cause a reduction in ethylene oxide production at later stages of catalyst life.

U.S. Pat. No. 4,074,660 issued Feb. 21, 1978, describes a process for cooling a high temperature reaction effluent to increase the heat recovery there from by cooling the effluent in a shell and tube heat exchanger having continuous tubes, with the shell being divided into two sections. In the first section, the effluent is cooled with water at a pressure that generates medium-pressure steam. In the second section, the effluent is cooled by water at a pressure that generates low-pressure steam or merely effects a preheating without vaporization. The system is described for use in waste-heat recovery from a high-temperature effluent such as the effluent from an ethyl benzene dehydrogenation reactor for the production of styrene. The temperature of that effluent is at least about 500° F., and is generally in the order from about 600° F. to about 2000° F. That patent does not provide a solution to the problem of recovering heat from a coolant at a temperature below 500° F. while generating sufficient steam in an existing conventional ethylene oxide plant with the existing coolant condensers.

EP No. 139,601, published Feb. 5, 1985 to Neel et al., describes a process for concentrating ethylene oxide solutions by steam distillation followed by multistage condensation in series connected heat exchangers. The so-described heat exchangers are designed for condensing the ethylene oxide solution rather than generating steam from the coolant for the ethylene oxide reactor.

A process has now been devised to recover residual heat in a conventional EO/EG plant designed for conventional catalyst(s) but utilizes improved catalyst(s) which also allows the plant to take optimum advantages of the improved activites and selectivities of the catalysts. The advantage of the present process is effected by the installation of auxiliary coolant condensing unit(s) to give a second, lower-pressure steam generation system and a change to a lighter coolant. Lower-pressure steam is additionally generated to be used in processes wherein a lower temperature would be adequate.

SUMMARY OF THE INVENTION

The present invention improves a process for cooling the coolant from an ethylene oxide reactor while generating steam from the heat conveyed by that coolant. The coolant is passed from the reactor to at least one first coolant condenser(s) in which at least part of the coolant vapor is condensed by exchanging heat with boiler feed water which is converted to medium-pressure steam; the vapor-liquid two-phase stream(s) coming out of the first coolant condenser(s) flows to a vapor-liquid separator whereby the coolant vapor is separated from the liquid coolant and said coolant vapor is passed to at least one second coolant condenser(s) in which the vapor is condensed by exchanging heat with boiler feed water which is converted to steam at a pressure lower than the steam generated by the first coolant condenser(s). Each of the said first coolant condenser(s) or second coolant condenser(s) can either be a single condenser or a group of condensers.

In a preferred embodiment of the invention, the liquid coolant coming out of said vapor-liquid separator flows through a "U" trap before flowing to coolant surge drum(s). The "U" trap has a sufficient height to insure that the coolant vapor flows to the second coolant condenser(s) while in the case of reactor runaway allows rapid relieving of the pressure in the reactor and thus prevent the system from being overpressured resulting in equipment damage.

Particularly, the present invention provides a modification for an ethylene oxide plant whereby it can operate using catalysts which are more active and having lower optimum operating temperatures than for which it was designed while generating additional (lower pressure) steam to meet the amount of the steam required for efficient operation of the plant. The conventional plant utilizes one coolant condensing system. The modification of the present invention is based on the installation of an additional coolant condensing unit(s) to provide lower pressure steam to be used in processes where the lower temperature and pressure would be adequate. This dual-level steam generation system provides increased total quantity of steam and can do so without need for coolant system vapor-side instrumentation.

This invention can provide a reduction in the minimum coolant temperature as much as 15° F. while providing a two-fold reduction in catalyst decline rate and 5% increase in average EO production rate.

The invention also provides an improved coolant condensing process which tends to automatically compensate for temperature changes as catalysts age and coolant temperatures increase. In such situations, the first coolant condenser(s) begin to carry more and more of the load. Thus no coolant system vapor-side instrument or controller is needed.

BRIEF DESCRIPTION OF THE DRAWINGS

Throughout FIGS. 1-2, the same reference numerals have been used for similar purposes, and accessories such as valves, pumps and control instruments not necessary for the purpose of understanding the present invention are not (all) shown.

DETAILED DESCRIPTION OF THE INVENTION

Figure 1:
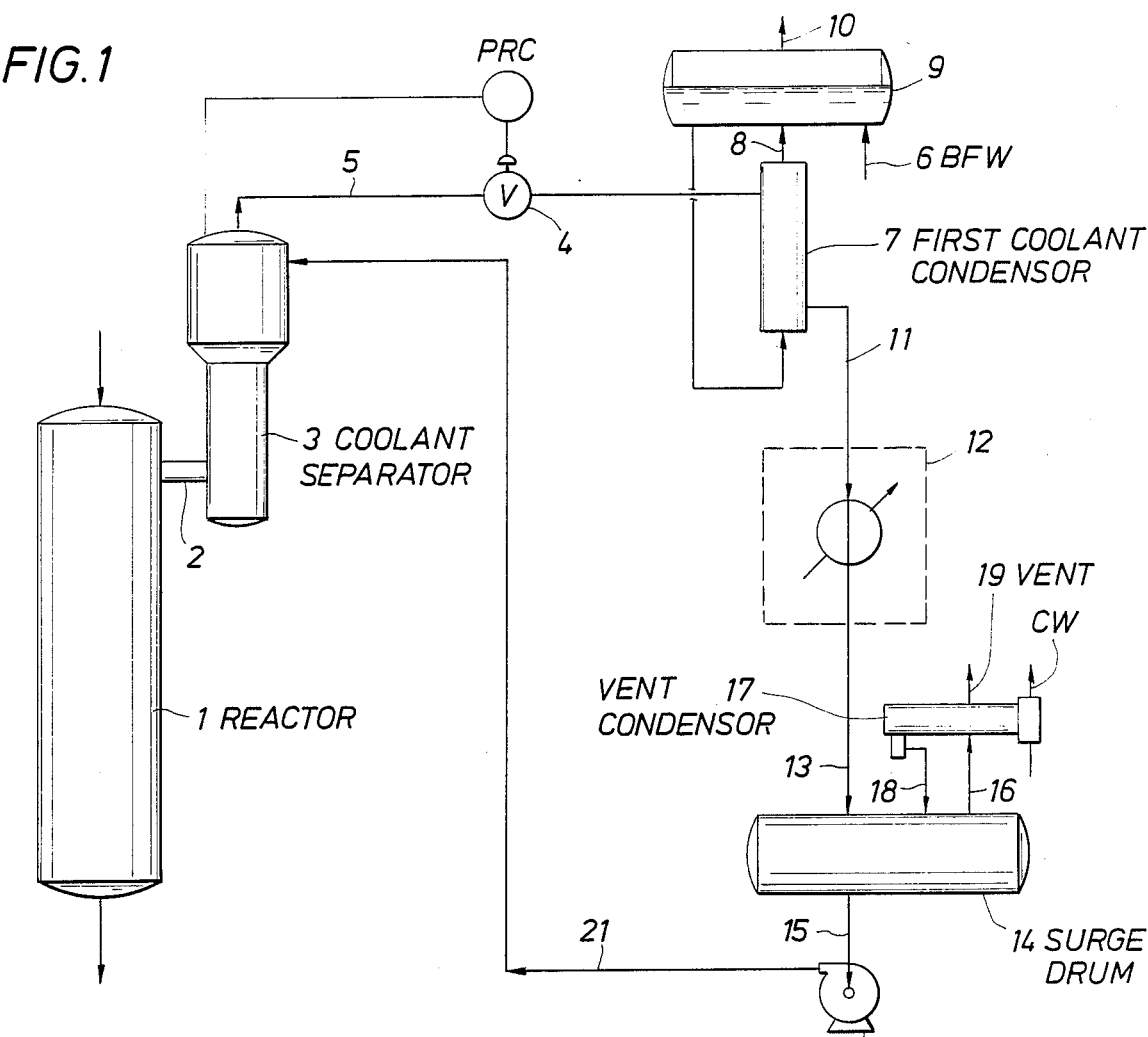
FIG. 1 is a schematic flow diagram of an EO coolant system with the auxiliary coolant system of the present invention shown within the dashed boundaries.

Referring to FIG. 1 of the drawings, the ethylene oxide reactor 1 is constructed as a large, fixed, tubesheet heat exchanger containing several thousand reactor tubes filled with the EO catalyst. Suitable catalyst includes an alumina-supported silver catalyst. Ethylene is reacted with oxygen over the catalyst to form EO. Some of the EO formed may isomerize to acetaldehyde (ACH) which, in turn, is rapidly oxidized to carbon dioxide and water, so that only traces of ACH are found in reactor product. Carbon dioxide and water are also formed in an ethylene oxidation competing with the main reaction. This reaction is suppressed by the use of a chlorine-containing catalyst moderator. The selectivity of the reaction is defined as the calculated mole percent of reacted ethylene which forms ethylene oxide. The heat of reaction is removed by boiling coolant on the shell side, thus maintaining a two-phase mixture in the shell. Hydrocarbons similar to kerosene, such as ISOPAR ® H (ASTM D 86 Distillation range is 346° F. IBP to 373° F. Dry Point, sold commercially by EXXON), are usually used as the coolant.

The vaporized coolant leaving the shell entrains several times its weight of liquid and flows to a coolant separator 3, in which, the vapor-liquid mixture passes through separating devices whereby the entrained liquid coolant is separated and returned to the reactor shell. The separated coolant vapor 5 flows to the first coolant condenser(s) 7 thereafter.

The coolant vapor is condensed in the coolant condenser 7 by water circulating from a steam drum 9. Makeup water is fed via stream 6. Thus medium-pressure steam 10 is produced. This steam is used as a heating source in various pieces of equipment in the EO/EG plant. Examples of the equipment which require steam as the heating source are: the pre-heater to the glycol reactor, the glycol dehydrator, the fractionation columns for mono-ethylene glycol, di-ethylene glycol and tri-ethylene glycol, the EO stripper, the EO purification column and the carbon dioxide stripper.

In a conventional plant, the liquid coolant condensate and any non-condensables 11 leaving the coolant condenser(s) 7 flow to a coolant surge drum 14 wherein the liquid coolant is separated from the non-condensables. The liquid coolant in lines 15 and 21 therefrom is returned to the coolant separator 3 and the reactor 1 thereafter by the coolant pump 20. The non-condensables flow to a vent condenser 17 and the liquid coolant 18 therefrom returns to the surge drum 14 and the non-condensable vapor 19 is vented.

When the reactor tubes in a conventional EO plant designed for a particular catalyst are loaded with an improved catalyst with higher activity and a lower optimum operating temperature, the temperature of the coolant in the coolant condenser 7 is therefore lower than that with said particular catalyst. The temperature difference ($\Delta T$) between the coolant vapor 5 and the generated steam 8 drops. Since the condensing surface in the condenser 7 is fixed in the conventional ethylene oxide plant designed for a particular catalyst, the amount of medium pressure steam generated 10 is therefore reduced. To avoid the cost of adding a steam generator, the reactor 1 has to be operated at temperatures higher than the optimum operating temperature of the improved catalyst in order to raise the coolant temperature high enough to provide sufficient $\Delta T$ and thereby generating enough medium pressure steam. When the reactor is not operated at the optimum temperature of the catalyst, the selectivity decline rate is accelerated. The average selectivity of the catalyst is therefore decreased and the average ethylene oxide production rate is thus significantly reduced.

In the improved process of the instant invention, the vapor-liquid two-phase streams 11 coming out of said first coolant condenser(s) 7 is passed through an auxiliary coolant condensing system located in section 12.

Figure 2:
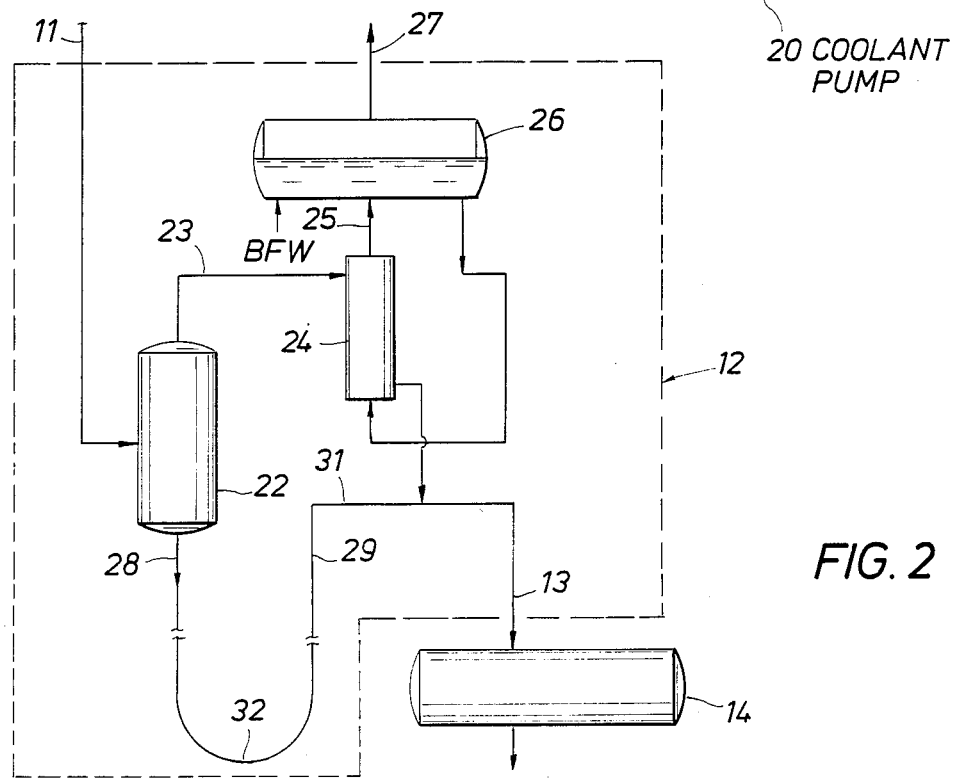
FIG. 2 is an enlargement of the section surrounded by the dashed lines in FIG. 1. It illustrates an auxiliary coolant condensing system involving the critical aspect of the present invention.

Referring to FIG. 2 which is the enlargement of section 12 surrounded by the dashed lines in FIG. 1, the vapor-liquid stream 11 flows to a vapor-liquid separator 22. The separated liquid coolant 28 flows via a "U" trap to the coolant surge(s) tanks 14 and the coolant vapor 23 passes through second coolant condenser(s) 24. The vapor therefrom flows to a lower-pressure steam drum(s) 26. The condensate from said second coolant condenser(s) 30 flows to said coolant surge(s) 14.

The vapro-liquid separator 22 can be any type of known out drums which will effectively separate liquid coolant from coolant vapor. It can be vertically positioned or horizontally positioned. It can be, but is not limited to, a cyclone, a centrifugal separator or a separator with demister.

In the separator 22, a pressure drop ($\Delta P$) is created. The "U" trap 29 has a sufficient height ($\Delta H$) between the bottom 32 and the top 31 to cause coolant vapor to flow upward to said second coolant condenser(s) 24. The height ($\Delta H$) is determined by the following relationship:

$$\Delta H \text{ (ft)} = 2.31 \times \Delta P \div \text{specific gravity of the coolant}$$

wherein 2.31 is the conversion factor for converting psi into feet of head (the difference in potential between two points positioned at different height in the flow system).

With the addition of the auxiliary coolant system 12, the reactor may be operated at lower and optimum temperatures. Although less medium pressure steam 8 is generated, the process provides lower pressure steam 27 which can be used for heating the fractional separation devices processes in the EO/EG plant where lower temperature is sufficient. Examples of fractional-separation devices which require lower temperatures comprise EO stripper, EO purification column and carbon dioxide stripper, etc. With the supplement of lower pressure steam, the overall need for the steam in EO/EG plant can be satisfied. The pressure of the medium-pressure steam 10 generated from the first condenser(s) is typically between about 150 psig to about 250 psig and suitably between about 175 psig to about 225 psig. The corresponding temperature of the medium-pressure steam generated is typically between 366° F. and 407° F. and suitably between 377° F. and 397° F.

The pressure of the lower-pressure steam 27 generated from the second coolant condenser(s) is typically between about 50 psig to about 150 psig and suitably between 100 psig and 140 psig. The corresponding temperature of the lower-pressure steam generated is typically from 298° F. to 366° F. and suitably between 337° F. and 360° F.

Without the modification, the dew point temperature (DPT) (443° F.) which is the temperature at which the coolant vapor begins to condense when entering the coolant condenser(s) 7 typically would be between about 430° F. and about 460° F., so that, it would provide sufficient ΔT for generating enough medium-pressure steam.

With the improvement of the present invention, the dew point temperature is typically kept at from about 400° F. to about 430° F.

The ΔP in the separator 22 is typically between about 1 psi to about 2 psi or suitably between about 1.3 and 1.8 psi.

The height of the "U" trap is typically from about 5 ft. to about 15 ft. and suitably from about 7 ft. to about 10 ft.

The modification also allows a reduction in the minimum coolant temperature as much as 15° F. The coolant used can be changed to a lower boiling hydrocarbon. Normally, EO plants use as coolant a kerosene or paraffinic hydrocarbon with a distillation range typically from 346° F. IBP to 373° F. Dry Point (ASTM D 86). In a specific embodiment of the invention, the coolant is changed to ISOPAR ® G (ASTM D 86 distillation range is 313° F. IBP to 345° F. End point; sold commercially by EXXON).

Since the catalyst is operated under optimum temperature, there is a reduction in selectivity decline rate which means the average EO production rate is thus higher.

As suggested above, the silver-based EO catalyst has a tendency towards steadily declining performance. Activity decline is accompanied by the yield decreases, requiring ever increasing support coolant temperatures and pressures to maintain the desired EO production rate. The support coolant temperature may have to be increased, e.g., up to 40° C. over the life of the catalyst. As the coolant vapor temperature increases, the first coolant condenser(s) carry more and more of the load. The auxiliary coolant condenser(s) generate less and less steam and may finally become unloaded, passing from the conditions for fresh catalysts to the condition for aged catalysts, operation of the condensation system is automatic with no great attention required. No coolant system vapor-side instrument or controller is needed.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

What is claimed is:

1. A process for the production of ethylene oxide by catalytic oxidation of ethylene with oxygen wherein steam is generated from the heat conveyed by the coolant for cooling the reactor, the improvement which comprises the steps of:
    (a) passing the coolant from the reactor to at least one first coolant condenser(s) wherein at least part of the coolant vapor is condensed by exchanging heat with boiler feed water to generate steam thereby producing a vapor-liquid coolant mixture; and
    (b) passing said vapor-liquid coolant mixture from said first coolant condenser(s) through a vapor-liquid separator and passing the vapor separated therefrom through at least one second condenser(s) wherein at least part of the vapor is condensed by exchanging heat with boiler feed water to generate steam at a pressure lower than the steam generated by said first coolant condenser(s).

2. The process as claimed in claim 1, wherein said reactor is loaded with an alumina-supported silver catalyst.

3. The process according to claim 2, wherein the liquid coolant from said vapor-liquid separator flows via a "U" trap to coolant surge tank(s); said "U" trap has a sufficient height to cause the coolant vapor to flow to the second coolant condenser(s) while in the case of reactor runaway allows rapid relieving of the pressure in the reactor.

4. The process of claim 2, wherein said coolant is a paraffinic hydrocarbon having distillation range about 313° F. IBP to 345° F. End Point by ASTM D 86.

5. The process of claim 2, wherein said vapor-liquid separator comprises a cyclone.

6. The process according to claim 3, wherein said vapor-liquid separator comprises a cyclone and said coolant is a paraffinic hydrocarbon having distillation range about 313° F. IBP to 345° F. End Point by ASTM D 86.

7. In a process for the production of ethylene oxide by catalytic oxidation of ethylene with oxygen using an alumina-supported silver catalyst wherein steam is generated from the heat conveyed by the coolant for cooling the reactor by the process comprising the steps of passing the coolant from the reactor to at least one first coolant condenser(s) wherein at least part of the coolant vapor is condensed by exchanging heat with boiler feed water to generate steam thereby producing a liquid-vapor coolant mixture, the improvement which comprises the steps of passing the vapor-liquid mixture coming out of said first coolant condenser(s) to a vapor-liquid separator whereby the liquid coolant is separated from the vapor coolant and is passed via a "U" trap to at least one coolant surge drum(s) and the vapor passes through at least one second condenser(s) wherein it is condensed by exchanging heat with boiler feed water to generate steam at a lower pressure than that generated by said first coolant condenser(s); wherein said "U" trap has a sufficient height to insure that the coolant vapor flows upward to said second coolant condenser(s).

8. In a process for the production of ethylene oxide by catalytic oxidation of ethylene with oxygen using an alumina-supported silver catalyst wherein steam is generated from the heat conveyed by the coolant for cooling the reactor by the process comprising the steps of passing the coolant from the reactor to at least one first coolant condenser(s) wherein at least part of the coolant vapor is condensed by exchanging heat with boiler feed water to generate steam thereby producing a liquid-vapor coolant mixture, the improvement which comprises the steps of passing the vapor-liquid mixture coming out of said first coolant condenser(s) through a cyclone operated vapor-liquid separator whereby the liquid coolant is separated from the coolant vapor and flows via a "U" trap to at least one coolant surge drum(s) and the vapor passes through a second condenser(s) wherein it is condensed by exchanging heat with boiler feed water to generate steam at a lower pressure than that of the steam generated by said first coolant condenser; wherein said "U" trap has a sufficient height to insure that the coolant vapor flows upward to said second coolant condenser(s) while in the case of reactor runaway allows rapid relieving of the pressure in the reactor; said improvement enabling the plant to operate utilizing an improved silver-based catalyst with a lower optimum operating temperature than that of the alumina-supported silver catalyst for which the plant was designed by recovering residual heat from the coolant in the form of steam.

* * * * *